United States Patent [19]

VandenBerg

[11] Patent Number: Plant 6,950

[45] Date of Patent: Jul. 25, 1989

[54] CHRYSANTHEMUM PLANT NAMED DELANO

[75] Inventor: Cornelis P. VandenBerg, Salinas, Calif.

[73] Assignee: Yoder Brothers, Inc., Barberton, Ohio

[21] Appl. No.: 218,982

[22] Filed: Jul. 14, 1988

[51] Int. Cl.[4] ..... A01H 5/00

[52] U.S. Cl. ..... Plt./82

[58] Field of Search ..... Plt./82

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Delano particularly characterized by its flat capitulum form; decorative capitulum type; dark red-purple ray floret color; diameter across face of capitulum of up to 12 cm at maturity; uniform eight week photoperiodic flowering response to short days; medium plant height when grown as a pinched disbudded pot mum; recommended as disbudded pot mum; and spreading and prolific branching pattern.

3 Drawing Sheets

The present invention comprises a new and distinct cultivar of Chrysanthemum, botanically known as *Dendranthema grandiflora,* and referred to by the cultivar name Delano.

Delano, identified as 84-258006, was originated from a cross made in a controlled breeding program in Salinas, Calif. in 1984.

The female parent of Delano was the cultivar identified as Favor, disclosed in U.S. Plant Pat. No. 5,227. The male parent of Delano was an unnamed seedling, identified as 81-D05003.

Delano was discovered and selected as one flowering plant within the progeny of the stated cross by Cornelis P. VandenBerg in February of 1985, in a controlled environment in Salinas, Calif.

The first act of asexual reproduction of Delano was accomplished when vegetative cuttings were taken from the initial selection in April of 1985 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Delano are firmly fixed and are retained through successive generations of asexual reproduction.

Delano has not been observed under all possible environmental conditions. The phenotype may vary significantly with variations in environment such as temperature, light intensity, and daylength.

The following observations, measurements and comparisons describe plants grown in Salinas, Calif. and Leamington, Canada, under greenhouse conditions which approximate those generally used in commercial greenhouse practice.

The following traits have been repeatedly observed are are determined to be basic characteristics of Delano, which, in combination, distinguish this Chrysanthemum as a new and distinct cultivar:

1. Flat capitulum form.
2. Decorative capitulum type.
3. Dark red-purple ray floret color.
4. Diameter across face of capitulum up to 12 cm at maturity.

5. Uniform eight week photoperiodic flowering response to short days.
6. Medium plant height, requiring 0 to 7 long days after pinch prior to short days and 1 application of 2500 ppm B-9 SP to attain a flowered plant height of 25 to 35 cm for year-round flowerings when grown as a pinched disbudded pot mum.
7. Recommended as disbudded pot mum.
8. Spreading and prolific branching pattern.

The accompanying photographic drawings show typical inflorescence and leaf characteristics of Delano, with the colors being as nearly true as possible with illustrations of this type.

Sheet 1 is a color photograph of Delano grown as a pinched disbudded pot mum.

Sheet 2 is a black and white photograph of three views of the inflorescence of Delano.

Sheet 3 is a black and white photograph showing the upper and under sides of the leaves of Delano at three stages of development (mature, intermediate and immature).

Of the commercial cultivars known to the inventor, the most similar in comparison to Delano is the cultivar Deep Luv, disclosed in U.S. Plant Pat. No. 5,777. Reference is made to attached Chart A, which compares certain characteristics of Delano to the same characteristics of Deep Luv.

Similar traits are capitulum form and type and flowering response period. The color of ray florets of Delano is much more dark red-purple than the red-purple color of Deep Luv. Delano has a more spreading and prolific branching pattern, a slightly larger diameter of capitulum and a larger plant height.

In the following description, color references are made to The Royal Horticultural Society Color Chart. The color values were determined on plant material grown in Salinas, Calif. on Mar. 14, 1988.

Classification:

*Botanical.*—*Dendranthema grandiflora,* cv. Delano.
*Commercial.*—Decorative disbus pot mum.

INFLORESCENCE

A. Capitulum:

*Form.*—Flat.
*Type.*—Decorative.

*Diameter across face.*—Up to 12 cm at maturity.

B. Corolla of ray florets:

*Color (general tonality from a distance of three meters).*—Dark red-purple.

*Color (upper surface).*—60A to 60B.

*Color (under surface).*—70B.

*Shape.*—*Flat, oblong.*

C. Corolla of disc florets:

*Color (mature).*—Closest to 154B.

*Color (immature).*—Closest to 144C.

D. Reproductive organs:

*Androecium.*—Present on disc florets only; no pollen.

*Gynoecium.*—Present on both ray and disc florets.

PLANT

A. General appearance:

*Height.*—Medium; 25 to 35 cm as a pinched disbudded pot mum, with 0 to 7 long days after pinch prior to short days and 1 application of 2500 ppm B-9 SP.

*Branching pattern.*—Spreading and prolific.

B. Foliage:

*Color (upper surface).*—147A.

*Color (under surface).*—147B.

*Shape.*—Lobed and slightly serrated.

CHART A

Comparison of Delano and Deep Luv

| Cultivar | Ray Floret Color | Capitulum Form and Type | Branching Pattern |
|---|---|---|---|
| Delano | Dark Red Purple | Flat Decorative | Spreading and prolific |
| Deep Luv | Red Purple | Flat Decorative | Semi-spreading |

| Cultivar | Diameter across face of capitulum | Plant height | Flowering response period |
|---|---|---|---|
| Delano | Up to 12 cm | Medium | 8 weeks |
| Deep Luv | 9 to 11 cm | Short | 8 weeks |

Comparisons of plants grown as pinched disbudded pot mums in Salinas, California

I claim:

1. A new and distinct Chrysanthemum plant named Delano, as described and illustrated.

* * * * *

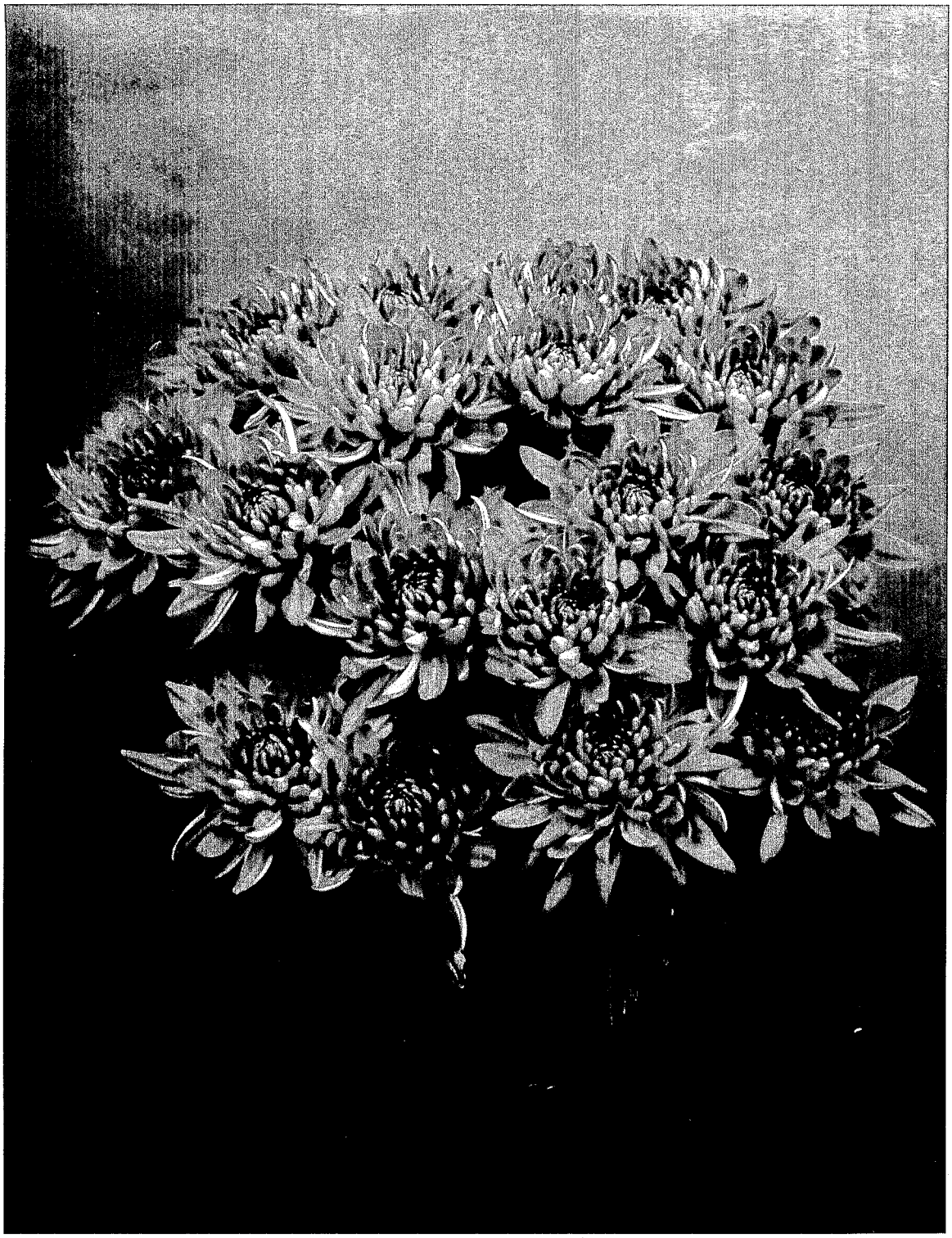

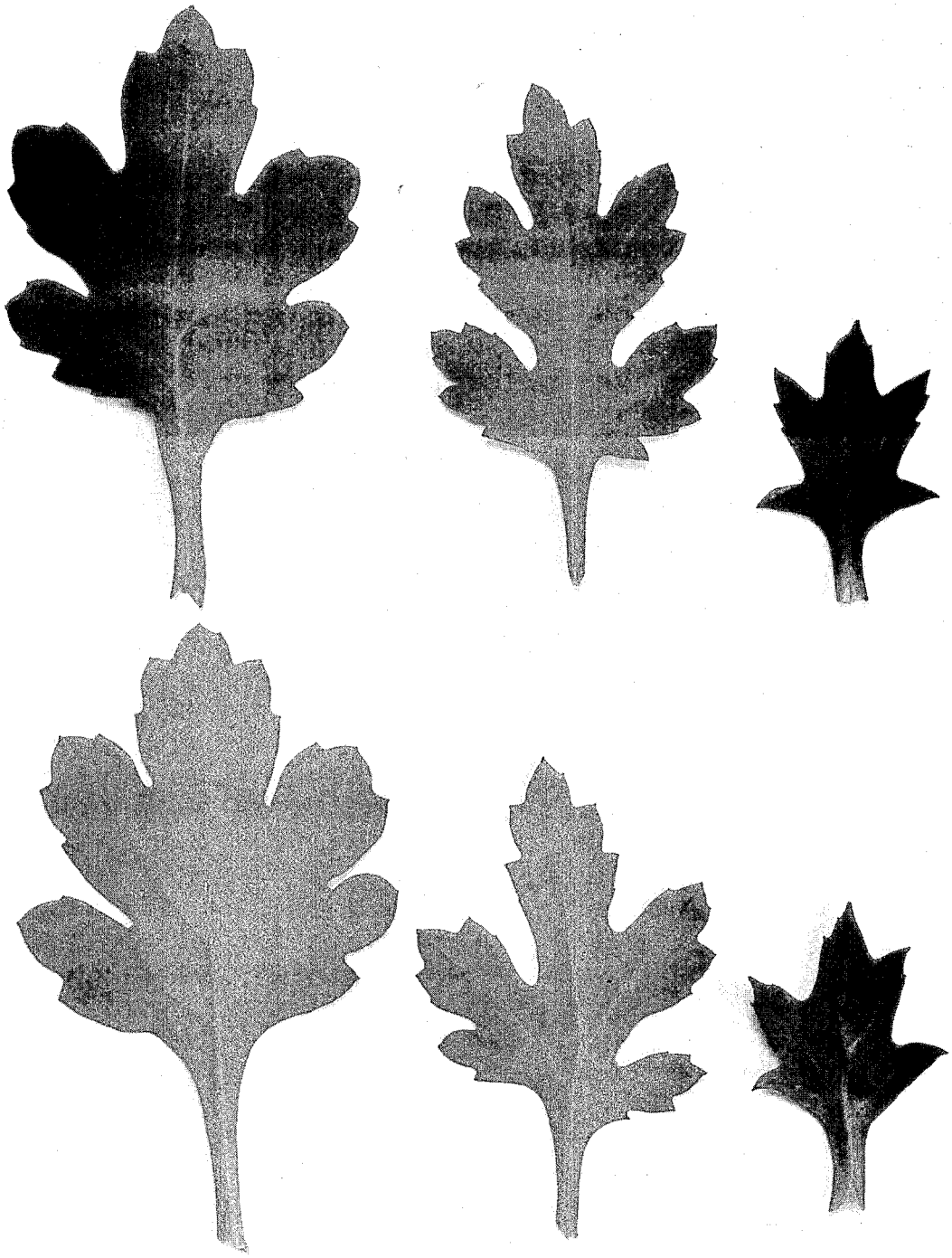

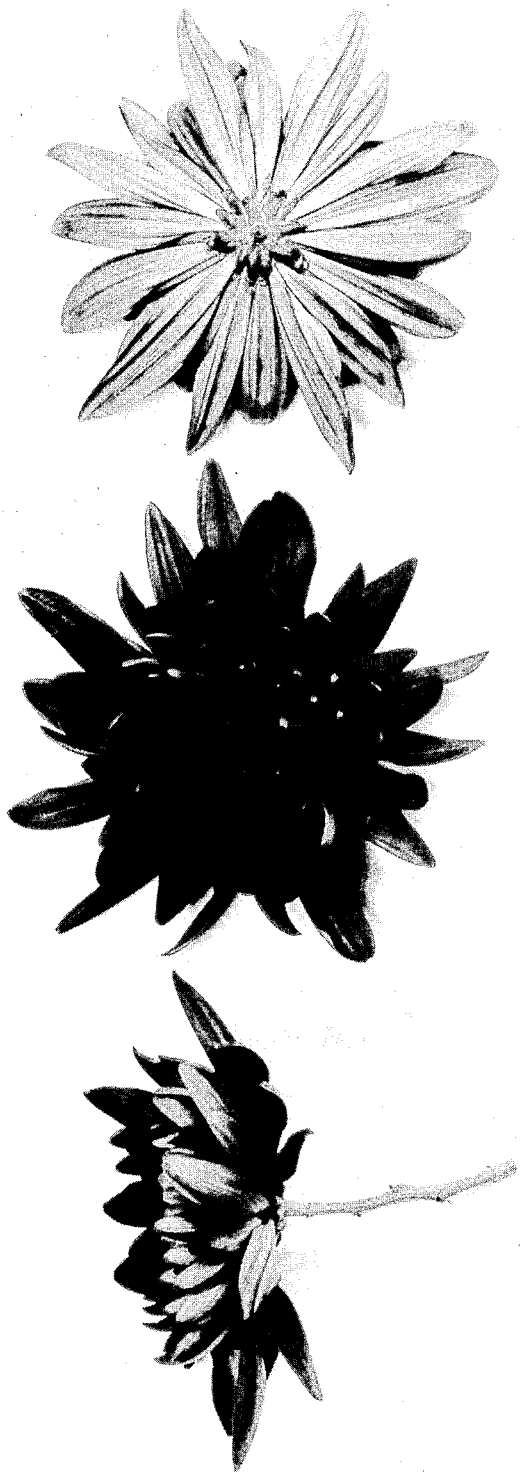

UNITED STATES PATENT AND TRADEMARK OFFICE

CERTIFICATE OF CORRECTION

PATENT NO. : Plant 6,950

DATED : July 25, 1989

INVENTOR(S) : Cornelis P. VandenBerg

It is certified that error appears in the above-identified patent and that said Letters Patent is hereby corrected as shown below:

Column 2, line 40, "disbus" should be changed to --disbud--.

Signed and Sealed this

Twelfth Day of March, 1991

*Attest:*

HARRY F. MANBECK, JR.

*Attesting Officer*

*Commissioner of Patents and Trademarks*